US006998121B2

(12) United States Patent
McMichael

(10) Patent No.: US 6,998,121 B2
(45) Date of Patent: Feb. 14, 2006

(54) METHOD OF TREATMENT OF CONNECTIVE TISSUE DISORDERS BY ADMINISTRATION OF STREPTOLYSIN O

(75) Inventor: John McMichael, Delanson, NY (US)

(73) Assignee: Milkhaus Laboratory, Inc., Providence, RI (US)

(*) Notice: Subject to any disclaimer, the term of this patent is extended or adjusted under 35 U.S.C. 154(b) by 496 days.

(21) Appl. No.: 10/349,606

(22) Filed: Jan. 23, 2003

(65) Prior Publication Data

US 2004/0146496 A1    Jul. 29, 2004

(51) Int. Cl.
A61K 38/47    (2006.01)
A61K 9/00     (2006.01)
A61K 47/00    (2006.01)

(52) U.S. Cl. .................... 424/94.61; 424/439; 424/400
(58) Field of Classification Search .............. 424/94.61, 424/400, 439
See application file for complete search history.

(56) References Cited

U.S. PATENT DOCUMENTS

| | | | |
|---|---|---|---|
| 5,240,846 A | 8/1993 | Collins et al. | |
| 5,292,498 A | 3/1994 | Boucher, Jr. | |
| 5,420,116 A | 5/1995 | Puchelle et al. | |
| 5,470,838 A | 11/1995 | von Borstel et al. | |
| 5,576,289 A | 11/1996 | McMichael | |
| 5,726,160 A | 3/1998 | McMichael | |
| 5,736,508 A | 4/1998 | McMichael | |
| 5,948,768 A | 9/1999 | McMichael et al. | |
| 5,955,442 A | 9/1999 | McMichael | |
| 6,096,721 A | 8/2000 | McMichael | |
| 6,303,127 B1 * | 10/2001 | McMichael et al. ..... | 424/198.1 |
| 6,447,820 B1 | 9/2002 | Niazi | |

FOREIGN PATENT DOCUMENTS

| | | |
|---|---|---|
| WO | WO 92/11016 | 7/1992 |
| WO | WO 93/12240 | 6/1993 |
| WO | WO 94/23048 | 10/1994 |
| WO | WO 95/25800 | 9/1995 |
| WO | WO 96/32138 | 10/1996 |
| WO | WO 96/40059 | 12/1996 |
| WO | WO 97/05195 | 2/1997 |

OTHER PUBLICATIONS

Alton, E.W.F.W. et al., "Noninvasive liposome-mediated gene delivery can correct the ion transport defect in cystic fibrosis mutant mice," *Chemical Abstracts*, 119:62 (1993) (*ABSTRACT 217089w*).
Badesch et al., "Continuous Intravenous Epoprostenol for Pulmonary Hypertension Due to the Scleroderma Spectrum of Disease, A Randomized, Controlled Trial," *Ann. Intern. Med.*, 132:425-434 (2000).
Baker, R.C., "Pitfalls in Diagnosing Acute Otitis Media," *Pediatric Annals*, 20:591-593, 596-598 (1991).
Barst et al., "A Comparison of Continuous Intravenous Epoprostenol (Prostacyclin) With Conventional Therapy for Primary Pulmonary Hypertension," *N. Eng. J. Med.*, 334:296-301 (1996).
Berkow, R. (Ed.), The Merck Manual of Diagnosis and Therapy, Sixteenth Edition, Merck Research Laboratories, Division of Merck & Co., Inc., Rahway, N.J. pp. 600-602 (1992).
Berman, S., "Otitis Media in Developing Countries," *Pediatrics*, 96:126-131 (1995).
Canonico, A.E. et al., "Expression Of A Cmv Promoter Driven Human A-1 Antitrypsin Gene In Cultured Lung Endothelial Cells And In The Lungs Of Rabbits," *Clin. Res.*, 39(2): 219A (1991).
Carman et al., "A Primary Care Approach to the Patient with Claudication," *Am. Fam. Physician*, 61:1027-1032 (2000).
Cunningham, M.W., "Pathogenesis of Group A Streptococcal Infections," *Clin. Microbiol.* 13:470-511 (2000).
Dagan, R. et al., "Treatment Failures in Otitis Media-What Can We Learn?," *Ear, Nose and Throat J.*, 77:16-21 (1998).
Dawson et al., "Cilostazol Has Beneficial Effects in Treatment of Intermittent Claudication," *Circulation*, 98:678-686 (1998).
DeGraves et al., "Economics of Mastitis and Mastitis Control," *The Veterinary Clinics of North America-Food Animal Practice Update on Bovine Mastitis*, 9:421-434 (1993).
Flotte, T.R., et al., "Stable *in vivo* expression of the cystic fibrosis transmembrane conductance regulator with an adeno-associated virus vector," *Chemical Abstracts*, 120:229(1994) (*ABSTRACT 46918e*).
Furth et al., "Gene Transfer into Somatic Tissues by Jet Injection," *Analytical Biochemistry*, 205:365-368 (1992).
Gent et al., A Randomised, Blinded, Trial of Clopidogrel Versus Aspirin in Patients at Risk of Ischaemic Events (CAPRIE), *Lancet*, 348:1329-1339 (1996).
Gardner et al., "Exercise Rehabilitation Programs for the Treatment of Claudication Pain: A Meta Analysis," *JAMA*, 274:975-980 (1995).
Goldhaber et al., "Low-Dose and Subsequent Peripheral Arterial Surgery in the Physicians' Health Study," *Lancet*, 340:143-145 (1992).
Harrison et al., "Structural Features of Interstitial Lung Disease in Systemic Sclerosis," *Am. Rev. Respir. Dis.*, 144:706-713 (1991).

(Continued)

Primary Examiner—Susan Coe
Assistant Examiner—Randall Winston
(74) Attorney, Agent, or Firm—Marshall, Gerstein & Borun LLP

(57) ABSTRACT

Method for administering streptolysin O to treat various connective tissue disorders in humans and animals such as Dupuytren's contracture, scleroderma, Peyronie's disease, mastistis in animals, and claudication due to peripheral arterial disease.

10 Claims, No Drawings

OTHER PUBLICATIONS

Hood et al., "Management of Intermittent Claudication with Pentoxifylline: Meta-Analysis of Randomized Controlled Trials," *CMAJ*, 155:1053-1059 (1996).

Janzon et al., "Prevention of Myocardial Infarction and Stroke in Patients with Intermittent Claudication; Effects of Ticlopidine. Results from STMS, the Swedish Ticlopidine Multicentre Study," *J. Intern.Med.*, 27:301-308 (1990).

Jarrow et al., "Peyronie's Disease and Radical Prostatectomy: Is There A Link?," *J. of Urology*, 158:1388-1390 (1997).

Karver, S.B., "Otitis Media," Ear, Nose and Throat Disorders, 25:619-632(1998).

Klein, J.O., "Otitis Media," Clinical Infectious Disease, 19:823-833 (1994).

Ledley, F.D., "Non-viral gene therapy," *Current Opinion in Biotechnology,* 5: 626-636 (1994).

Ledley, F.D., "Nonviral Gene Therapy: The Promise of Genes as Pharmaceutical Products," *Human Gene Therapy* 6: 1129-1144 (Sep., 1995).

Marshall, E., "Gene Therapy's Growing Pains," *Science,* 269: 1050-1055 (1995).

Patterson et al., "Value of a Supervised Exercise Program for the Therapy of Arterial Claudication," *J. Vasc. Surg.*, 25: 312-319 (1997).

Razin et al., "Protein Kinases C-β and C-ε Link the Mast Cell High-Affinity Receptor for IgE to the Expression of c-*fos* and c-*jun,*" *Proc. Natl. Acad, Sci. (USA)*, 91:7722-7726 (1994).

Rosenfeld, M.A. et al., "Adenovirus-Mediated Transfer of a Recombinant α1-Antitrypsin Gene to the Lung Epithelium in Vivo," *Science,* 252: 431-434(1991).

Rosenfeld, J. et al., "Acute Otitis Media in Children," *Primary Care; Clinics in Office Practice,* 23(4):677-686 (1996).

Ruiz et al., "Streptolysin O and Adherence Synergistically Modulate Proinflammatory Responses of Keratinocytes to Group A Streptococci," *Mol. Microbiol.* 27:337-346 (1997).

Schrager et al.,"Hyaluronic Acid Capsule Modulates M Protein-Mediated Adherence and Acts as a Ligand for Attachment of Group A *Streptococcus* to CD44 on Human Keratinocytes," *J. Clin. Investig.* 101:1708-1716 (1998).

Silver et al., "Evaluation and Management of Scleroderma Lung Disease Using Bronchoalveolar Lavage," *Am. J. Med.*, 88:470-476 (1990).

Unemori et al., "Relaxin Modulates Synthesis and Secretion of Procollagenase and Collagen by Human Dermal Fibroblasts," *J. Biol. Chem.*, 265:10681-10685 (1990).

Visa et al., "The Value of Fasciectomy in the Surgical Approach of the Dupuytren's Disease," *Romanian Journal of Hand and Reconstructive Microsurgery*, 5:9-13 (2000).

Wallaert et al., "Subclinical Pulmonary Involvement in Collagen-Vascular Diseases Assessed by Bronchalveolar Lavage," *Am. Rev. Respir. Dis.*, 133:574-580 (1986).

White et al., "Cyclophosphamide is Associated with Pulmonary Function and Survival Benefit in Patients with Scleroderma and Alveolitis," *Ann. Intern. Med.*, 132:947-954 (2000).

Siebold et al., "Recombinant Human Relaxin in the Treatment of Scleroderma, A Randomized, Double-Blind, Placebo-Controlled Trial," *Ann. Intern. Med.*, 132:871-879 (2000).

Murinda et al., "Isolation of Mastitis and Food-Borne Pathogens in Bulk Tank Milk and Fecal Samples from Cull Dairy Cows," Schrick et al., *Department of Animal Science Annual Report*, The University of Tennessee, Knoxville, in press.

Taranta et al., "The Relationship of Sydenham's Chorea to Infection with Group A Stretococci," *Am. J. Med.*, 20:170-175 (1956).

Kiessling et al., "Antineuronal Antibodies in Movement Disorders," *Pediatrics*, 92:39-43 (1993).

Askanas et al., "A New Program for Investigating Adult Human Skeletal Muscle Grown Aneurally in Tissue Culture," *Neurology*, 25:58-67 (1975).

International Search Report corresponding to International Patent Application Serial No. PCT/US04/01887 dated Aug. 26, 2004, 2 pages.

* cited by examiner

METHOD OF TREATMENT OF CONNECTIVE TISSUE DISORDERS BY ADMINISTRATION OF STREPTOLYSIN O

FIELD OF THE INVENTION

The present invention relates to methods for treatment of connective tissue disorders by administration of streptolysin O.

BACKGROUND OF THE INVENTION

Connective tissue is the material between the cells of the body that gives tissues form and strength. This "cellular glue" is also involved in delivering nutrients to the tissue, and in the special functioning of certain tissues. Connective tissue is made up of dozens of proteins, including collagens, proteoglycans, and glycoproteins. The combination of these proteins can vary between tissues. The genes that encode these proteins can harbor defects or mutations, which can affect the functioning of certain properties of connective tissue in selected tissues. As described below, there are a number of different disease states where connective tissue play an important role in the pathological manifestations of the particular disease including Dupuytren's contracture, scleroderma, Peyronie's disease, claudication due to peripheral arterial disease and mastitis in animals.

The present invention relates to methods for treatment of connective tissue disorders including Dupuytren's contracture, scleroderma, Peyronie's disease, and lower limb claudication. These diseases take an enormous toll on people's ability to work, perform physical and sexual activity, maintain normal living standards, and perform everyday activities. In addition, post chronic mastitis infections in bovines have huge economic implications on the viability of livestock and the food supply, specifically the dairy industry.

Peripheral arterial disease (PAD) involves damage to or blockage of the blood vessels distant from the heart (usually in the arms and the legs) and includes several clinical syndromes in the extremities characterized by pain, inflammation, and ischemic damage to soft tissues from partial or complete occlusion of major arteries. The most characteristic symptom of PAD is intermittent claudication, which is described as cramping, aching, and numbness of the extremities induced by exercise. Intermittent claudication subsides by ending the exercise regiment. The symptoms of claudication result from artherosclerosis, which is a condition where plaque consisting of cholesterol, fats, calcium, and fibrin (blood clotting agent) build up on the inside of the artery wall. The artery wall consists of three layers: a layer of connective tissue, a second layer of smooth muscle cells and elastic connective tissue, and a third layer of endothelial cells. Damage to these cells leads to thrombocyte adhesion, aggregation, and formation of thrombi or intima in the arterial wall. This formation allows monocytes to stick to the arterial wall and maturate into macrophages, while recruiting LDL cholesterol to create a foam cell formation or fatty streaks. This interruption in the arterial endothelial lining causes platelets to become activated and recruit smooth medial muscle cells into the initma leading to connective tissue proliferation and lipid uptake. This cycle of inflammation and proliferation of connective tissue in the arterial wall of the blood vessel leads to narrowing of the arterial lumen, restricting blood flow.

The risk factor for artherosclerosis in the peripheral arteries of the legs and arms are the same as those for atherosclerosis in the coronary arteries. Smoking, diabetes, high blood pressure, and high cholesterol lead to the development of plaque. Most people with atherosclerosis in the leg arteries have no symptoms because the body develops small blood vessels (collateral vessels) around the blockage. With sustained activity, the collateral vessels are unable to supply enough oxygen to the leg's muscles and therefore, the pain is associated in the calf, thigh or buttocks muscles. In more advanced claudication, pain can occur even while one is at rest. If this symptom is left untreated, the lack of circulation may result in sores on the legs and feet, and the tissue can become gangrenous, requiring amputation.

Claudication is often a sign of artherosclerosis of both the coronary and carotid arteries. In treating atherosclerotic diseases, physicians should focus on evaluation, risk factor modification (quitting smoking and reducing cholesterol), and exercise (stimulate carotid arteries and condition muscles) (see Carmen et al., *Am Fam. Physician* 61:1027–1034 (2000); Gardner et al., *JAMA* 274:975–980 (1995); Patterson et al., *J. Vasc. Surg.* 25:312–319 (1997)). Antiplatelet agents, which prevent the recruiting activities of platelet cells, such as aspirin, ticlopidine, or clopidogrel, reduce the risk of vascular death, myocardial infarction, and stroke as much as 24% (see Goldhaber et al., *Lancet* 340:143–145 (1992); Janzon et al., *J. Intern. Med.* 227: 301–308 (1990); *Lancet* 348:1329–1339 (1996)). The combination of exercise and the drug pentoxifylline appears to reduce claudication (Hood et al., *CMAJ* 155:1053–1059 (1996)). The drug, Cilostazol, a phosphodiesterase inhibitor that suppresses platelet aggregation and arterial vasodilator, increases the amount and quality of exercising a patient can perform to overcome claudication (Dawson et al., *Circulation* 98:678–686 (1998)). Although these medical measures show some improvement of claudication, there remains a need in the art for methods to better treat peripheral arterial disease.

Dupuytren's contracture is a painless thickening and contracture of tissue beneath the skin on the palm of the hand. The cause of the contracture is unknown, but minor trauma and genetic predisposition may play a role. One or both hands may be affected. The ring finger is affected most often, followed by the little, middle and index finger. A small, painless nodule develops in the connective tissue and eventually develops into a cord-like band. Gradually, other nodules may develop and extend a contracture across the first joint into the finger. The overlying skin begins to pucker, and rough cords of tissue extend into the finger. As the process continues, these cords tighten and pull the finger in toward the palm. The ring finger is usually affected first, followed by the little, long and index fingers. The problem is not pain, but the restriction of motion and the deformity it causes. The progress of the disease is often sporadic and unpredictable. Exactly what triggers the formation of nodules and cords is unknown. As the disease progresses, the diseased nodules wraps itself around and between the normal tissue.

The incidence increases after the age of 40, and men are affected more often than women. Interestingly, the risk factors are associated with alcoholism, epilepsy, pulmonary tuberculosis, diabetes, and liver disease. Treatment for this disease can include exercises to stretch the diseased tissue, warm water baths, or splints. Often, these measures only slow the contracture, but do not cure the contracture. If the contracture continues, surgery may be performed to release the contracture, depending upon the severity of the condition. Several techniques including fasciectomy, dermofasciectomy, fasciotomy, and amputation are used. Fasciectomy is a corrective surgery performed by removing the fascia tissue and stitching up the wound in a zig-zag manner (See Visa et al., *Romanian Journal of Hand and Reconstructive Microsurgy* 5:9–13 (2000)). Dermofasciectomy is a corrective procedure of an advanced state of Dupuytren's contracture, where the skin and the fascia bands and nodules are removed. The removed skin is replaced by a skin graft. Fasciotomy is a medical procedure for elderly patients unfit for complicated surgery where the bands are cut. Finally, in rare cases, fingers in which the bands have returned many times and previous nerve and tissue damage exist, amputation of the finger is an option. While surgery usually restores normal movement to the fingers, the disease can reoccur following surgery and the risk of nerve damage increases after each surgery. Therefore, there remains a need for a less drastic method for treating Dupuytren's contracture.

Peyronie's disease is a disorder of the connective tissue within the penis that can cause curvature during erection. The disease is characterized by a plaque, or a hard lump, that forms in the erectile tissue of the penis. It begins as a localized inflammation and can then mature into a hardened scar. The cause of Peyronie's disease can be attributed to the septum connective tissue, which lines the inner membrane of each erectile cylinder that runs the length of the penis and attaches at the top and bottom of the penis. If the penis is abnormally squeezed or flexed, the area where the septum attaches to the elastic fibers may over-stretch, injuring the lining of the erective chamber and rupturing small blood vessels. In older men, diminished elasticity, disease of the arteries, diabetes, or radical prostatectomy further increase the chance of injury. In fact, Peyronie's disease is diagnosed in only 26 out of 100,000 men each year; however, the ratio increases to 3 out of 64 patients who develop Peyronie's disease after a radical prostatectomy (Jarrow et al., *J. of Urology* 158:1388–1390 (1997)).

Men with Peyronie's disease usually seek medical attention because of painful erections or difficulty with intercourse. The goal of any treatment is to keep the Peyronie's patient sexually active. Providing education about the disease and its course is often all that is required. There is no strong evidence that any treatments other than surgery are effective. Experts usually recommend surgery only in long-term cases where the disease has stabilized and where the deformity prevents intercourse. The two most common surgical methods are removal or expansion of the plaque followed by a placement of a patch of skin or artificial material and removal of pinching tissue from the side of the penis. Both procedures have the disadvantage of side effects including loss of erectile function or shortening of the erect penis. Often, the plaques of Peyronie's disease shrinks or disappears without treatment over a 6–15 month period, and thus, medical experts suggest waiting 1 to 2 years before attempting to correct it surgically. Spontaneous improvement in the disease is seen in 60–70% of patients.

Simple medical treatments have not been clinically proven. Some researchers have given men with Peyronie's disease vitamin E orally in small-scale studies, but these studies have proven inconclusive. Also, similar inconclusive success has been attributed to oral application of para-amino benzoate, a substance belonging to the family of B-complex molecules. Injection treatment with agents such as dimethyl sulfoxide, steroids, and calcium channel blockers directly into the plaques is used by some doctors, but none of these techniques have produced convincing results. The only medical treatment proven to be effective is Tamoxifen, which can relieve the pain and limit any subsequent bending of the penis. The disadvantage of Tamoxifen is that Peyronie's disease must be diagnosed early for the most effective use of the drug and therefore, there remains a desire in the art for methods for the treatment and prevention of Peyronie's disease.

Scleroderma is an autoimmune disease of the connective tissue, which affects many body systems such as the gastrointestinal tract, the respiratory, renal, cardiovascular, and genitourinary systems, but is primarily characterized by thickening and tightening of the skin. This disease may either be visible, as when the skin is affected, or invisible, as when only internal organs are involved, but is usually a highly-individualized disease wherein its involvement may range from mild symptoms to life-threatening symptoms. The symptoms result from progressive tissue fibrosis and occlusion of the microvasculature by excessive production and deposition of types I and II collagens. Other macromolecules found in connective tissue (e.g., glycosaminoglycans, tenascin, fibronectin) increase in production due to inflammation of the area experiencing fibrosis. The vascular alternations show a predilection for affecting the small arteries, arterioles, and capillaries. The small vessel cytoskeleton is affected by structural defects that lead to collapse. Next, the tight junctions become altered and are no longer functional, allowing the endothelium to slip into the vessel lumen.

An estimated 300,000 persons in the United States have scleroderma with more women (4 times more) than men developing the disease usually between the ages of 20 to 50. Symptoms of scleroderma include one or more of the following: Raynaud's Phenomenon (abnormal sensitivity to cold in the extremities), swelling of the hands and feet, pain and stiffness of the joints, thickening of the skin, joint contractures, digestive system and gastrointestinal tract problems, Sjogren's Syndrome (dry mucus membranes), oral, facial and dental problems, kidney, heart, and lung involvement, and non-specific symptoms such as extreme fatigue, generalized weakness, weight loss, and vague aching of muscles, joints and bones. The most serious side effect of scleroderma is pulmonary hypertension, and its complications are the most frequent causes of mortality. For example, the lungs are affected in 70–80% of patients, and develop either fibrosis or change in the blood vessels, which leads to increased pressure in the pulmonary arteries (Harrison et al., *Am. Rev. Respir. Dis.* 144:706–713 (1991); Silver et al., *Am. J. Med.* 88:470–476 (1990)). The fibrosis usually starts with an increase in lung fiber density near the posterior (back) regions of the lungs. Later stages of fibrosis are characterized by the emergence of a network of fibrous lines. These fibrous lines eventually develop into regions containing large numbers of small cysts. The end-stage effect is sometimes referred to as "honeycombing" and is non-reversible (Wallaert et al., *Am. Rev. Respir. Dis.* 133:574–580 (1986)).

The goal for treating scleroderma is to prevent further complications (i.e. fibrosis) and reduce morbidity if complications exist. Primary treatment consists of inhibiting the immune system alterations, which may be responsible for the wide variety of systemic morbidity associated with this disease. Skin thickening can be treated with D-penicillamine and methotrexate, which both increases the effects of immunosuppressants and slows down the formation of collagen. The experimental drug relaxin has also shown promise reducing the extent and severity of skin thickening in patients with diffuse scleroderma (Seibold et al., *Ann. Intern. Med.* 132:871–879 (2000)). Relaxin attenuates the actions of profibrotic cytokines including transforming growth factor-$\beta$ and interleukin-1$\beta$, and increases secretion of dermal fibroblast collagenase, while reducing levels of tissue inhibitor of metalloproteinase (Unemori et al., *J. Biol. Chem.*

265:10681–10685 (1990)). Raynaud phenomenon can be treated with calcium blockers or topical nitrates. Gastrointestinal symptoms may be treated with antacids, pump inhibitors, and laxatives. More severe complications, like fibrosis in the lungs or pulmonary hypertension, require more drastic measures. For example, scleroderma and alveolitis (hypersensitive inflammation of alveolar cells in the lung) can cause severe damage to lung tissues. Treatment with experimental drugs such as cyclophosphamide work to inhibit inflammation, but is not effective against only scleroderma in the lungs. Rather, both sets of symptoms are required (White et al., *Ann. Intern Med.* 132:947–954 (2000)). Pulmonary hypertension is a relatively common complication of systemic sclerosis with a lack of viable treatment options and a high mortality rate. In light of these factors, the use of intravenous epoprostenol has shown some promise (Badesch et al, *Ann. Intern. Med.* 132:425–434 (2000)), but may have limited applicability due to possible acute and potentially fatal side effects such as pulmonary edema in patients suffering with veno-occlusive disease as well as scleroderma (Barst et al., *N. Eng. J. Med.* 334: 296–301 (1996)). Many of these treatments are in their experimental stages, and the current treatments for the various scleroderma complications either cause the patients to experience severe side effects, place them at risks for further complications or require a unique set of symptoms to provide adequate treatment. Thus, there remains a need in the art for improved methods for treating scleroderma.

Post chronic mastitis infection is a connective tissue disorder that can prevent adequate lactation of bovines. Mastitis is an inflammation of the udder that affects a high proportion of dairy cows throughout the world. There are three major types of mastitis, corresponding to three distinct stages of development. Acute mastitis is generally characterized by redness, heat, pain, hardness or swelling accompanied by fever, a loss of appetite, and lower milk production. There are two stages during acute mastitis including (1) the inflammatory stage where there is no infection and few to no lumps in the teats; (2) the infection stage where pus is generated and lumps begin to form. Bacteria such as *Escherichia coli, Streptococcus dysgalactiae,* coagulase-negative staphylococci, *Staphylococcus aureus, Streptococcus uberis,* colorless algae and corneybacterium can cause the initial infection via numerous vectors such as flies, flowing water, standing water, water tanks, water runoff from silage, well water, manure, teat dip containers, milking machine liners, teat end swabs and feed troughs. These bacteria are able to invade the mammary gland, multiply therein, and produce harmful substances that result in an inflammatory response. Once infection begins, the teats can become so infected that the milk first becomes yellow and then watery. After infection, chronic mastitis can occur which is the after-effect of repeated bouts of mastitis at the level of the teat where humps, lesions, hardenings, damaged teats, lost quarters, nodularthelitis, and a drop in milk production occur.

The focus of treatment is dependent upon the level of infection and how many repeat occurrences of mastitis have occurred. It is important to diagnose mastitis early in the infection. Chronic mastitis is the most critical to prevent. Animals with chronic mastitis often acquire permanent damage to the teat and the bovine loses productivity and is unable to release milk at a sufficient level from the damaged teat.

Mastitis is difficult to control since several bacteria have the ability to infect the udder. Even well managed dairy herds that utilized the most recent and most effective mastitis control measures witness a high rate of infection in the first 90 days of lactation (Schrick et al., *Department of Animal Science Annual Report*, The University of Tennessee, Knoxville, in press). Mastitis has been described as the most economically imposing disease facing dairy producers in the United States, costing an estimated $2 billion annually (DeGraves and Fetrow, *The Veterinary Clinics of North America-Food Animal Practice Update on Bovine Mastitis* 9:421–434 (1993)). Thus, there remains in the art the need for treatment that will allow bovines to continue to exhibit productive milk even after damage to the udder has occurred due to complications from chronic mastitis.

Streptolysin O is one of a group of filterable hemolysins derived from Group A beta-hemolytic streptococci. Specifically, streptolysin O is a 60-kD peptide, which is hemolytic in its reduced state, but is inactivated upon oxidation. Group A streptococci produce streptolysin O. It is thought that induction of a pro-inflammatory response in keratinocytes (skin cells) is associated with adherence of streptococci and their production of streptolysin O (Ruiz et al., *Mol. Microbiol.* 27:337–346 (1997); Cunningham, M. W., *Clin. Microbiol.* 13:470–511 (2000)). Specifically, the hyaluronic acid capsule of group A streptococci may be an important adherence factor since it binds to CD44 on epithelial cells (Schrager et al., *J. Clin. Investig.* 101:1708–1716 (1998)). Steptolysin O may also interact with CD-44 receptors on keratinocytes and dissolve collagen to allow streptococci to get in the blood stream. Streptolysin O is used in the art generally as an analytical reagent for permeabilizing cells (e.g. Razin et al., *Proc. Nat'l. Acad. Sci. (USA)* 91:7722–7726 (1994). Co-owned U.S. Pat. Nos. 5,576,289 and 5,736,508 disclosures are hereby incorporated by reference. U.S. Pat. No. 5,576,289 discloses the use of streptolysin O in methods for treating disease states characterized by motor deficit. U.S. Pat. No. 5,736,508 discloses the use of streptolysin O in methods for treating scarring. No disclosure, however, is made of an utility wherein streptolysin O is used to treat connective tissue disorders such as Dupuytren's contracture, scleroderma, Peyronie's disease, mastistis in animals, and claudication due to peripheral arterial disease.

Despite these recent applications of streptolysin O, there remains a desire to use streptolysin O to remedy other circulatory and muscle disorders including connective tissue disorders. Moreover, drastic measures for treating a connective tissue disorder include surgery that often leave large amounts of scarring tissue. Accordingly, there remains a desire in the art for improved treatment of various connective tissue disorders by administration of compounds that are relatively inexpensive, safe without accompanying side effects, and are easily administered.

SUMMARY OF THE INVENTION

The present invention provides methods for treating connective tissue disorders by administering streptolysin O. Specifically, the invention provides methods for alleviating symptoms of a connective tissue disorder such as Dupuytren's contracture, scleroderma, Peyronie's disease, mastitis in animals, and claudication due to peripheral arterial disease by administering to a patient in need thereof, streptolysin O in an amount effective to treat one or more symptoms of the connective tissue disorder.

Specifically, methods of the invention comprise administration to a patient suffering from a connective tissue disorder such as Dupuytren's contracture, scleroderma, Peyronie's disease, mastistis in animals, and claudication due to peripheral arterial disease, an effective amount of streptolysin O. The precise dose will vary among patients and may readily be determined by those of ordinary skill in the art. Nevertheless, streptolysin O is preferably administered in a amount ranging from about 0.0032 to 50 units (2 units/0.05 ml) per day and is preferably formulated in a liquid vehicle and provided at a concentration of approximately 4 units as a single drop. A single drop of streptolysin O is within the range of 0.05 to 10 units. More preferably, a drop of streptolysin O is in the amount of 2 units as a single drop. Streptolysin O is more preferably administered in an amount ranging from about 0.01 to 10 units per day or even more preferably administered in an amount ranging from about 0.1 to 8 units per day. A preferred route of administration is sublingually, but other routes, bucal, oral drench, subcutaneous, intradermal, intramuscular, intrathecal, intravenous, inhalation or topical, are expected to work.

The invention also provides a pharmaceutical composition of streptolysin O for administering to a subject, or patient for alleviating symptoms of a connective tissue disorder such as Dupuytren's contracture, scleroderma, Peyronie's disease, claudication due to peripheral arterial disease, and mastitis wherein the streptolysin O is in an amount effective to treat one or more symptoms of said connective tissue disorder in combination with pharmaceutically-acceptable excipients. Streptolysin O may be formulated in a number of pharmaceutically-acceptable excipients including, but not limited to, water, saline, albumin, dextrose or any other pharmaceutically acceptable excipient known in the art. The streptolysin O is preferably administered in a dosage amount ranging from about 0.0032 to 50 units (2 units/0.05 ml) per day and is preferably formulated in a liquid vehicle and provided at a concentration of approximately 4 units as a single drop. A single drop of streptolysin O is within the range of 0.05 to 10 units. More preferably, a drop of streptolysin O is in the amount of 2 units as a single drop. Streptolysin O is more preferably administered in an amount ranging from about 0.01 to 10 units per day or even more preferably administered in an amount ranging from about 0.1 to 8 units per day. A preferred route of administration is sublingually, but other routes, such as bucal, oral drench, subcutaneous, intradermal, intramuscular, intrathecal, intravenous, inhalation or topical, are expected to work.

DETAILED DESCRIPTION

The present invention provides methods for treating patients with symptoms of connective tissue disorders by any variety of modes of administration including, but not limited to, topical, sublingual, bucal, oral drenching, inhalation, subcutaneous, intrathecal, intramuscular, intradermal, or intravenous administration of a small amount of streptolysin O in a pharmaceutically acceptable excipient including water, saline, albumin, and dextrose. Specifically, the invention provides methods for treating Dupuytren's contracture including, but not limited to, treating the symptoms of thickening and contracture of the tissue beneath the skin of the palm of the hand and the limited everyday function with the hands.

The present invention also provides methods for treating claudications due to peripheral arterial disease by administration of a small amount of streptolysin O. Methods of the invention are also useful for treating symptoms of peripheral arterial disease including, but not limited to, the intermittent claudication symptoms such as cramping, aching, numbness, lack of circulation, and/or pain of the extremities.

The present invention also provides methods for treating patients with symptoms of Peyronie's Disease by administration of a small amount of streptolysin O. Methods of the invention are also useful for treating Peyronie's disease complications sufficient to treat symptoms of Peyronie's Disease including, but not limited to, painful erections or difficulty with intercourse.

The present invention also provides methods for treating patients with symptoms of scleroderma by administration of a small amount of streptolysin O. Methods of the invention are also useful for treating scleroderma complications, including, but not limited to, Raynaud's Phenomenon, swelling of the hands and feet, pain and stiffness of the joints, thickening of the skin, joint contracture, digestive and gastrointestinal tract problems, Sjogen's Syndrome, facial and dental problems, kidney disease, heart disease, lung disease, extreme fatigue, generalized weakness, weight loss, vague aching of muscles, joints, and bones, and pulmonary hypertension.

The present invention also provides methods for treating symptoms of chronic mastitis in bovines by administration of a small amount of streptolysin O. Methods of the invention are also useful for treating mastitis complications characterized by redness, heat, pain, hardness or swelling accompanied by fever, a loss of appetite, and lower milk production of the bovine.

The following Examples illustrate the methods of the invention with respect to treatment of connective tissue disorders, and, in particular, with respect to preferred methods of treating

EXAMPLE 1

An 85-year old female patient suffered from calf pain due to peripheral arterial disease. She began treatment with one drop (2 units/0.05 ml) of streptolysin O two to four times daily by sublingual administration. Before treatment, she could only walk three minutes without experiencing pain in her calf. With treatment, she has been able to walk nine minutes without pain in her calf.

EXAMPLE 2

An 80-year old female patient suffered from lower extremity pain due to peripheral arterial disease on her right side. She began a treatment regimen of one drop (2 units/ 0.05 ml) of streptolysin O four times daily by sublingual administration. With this treatment regimen, her pain has been relieved.

EXAMPLE 3

A 72-year old male was diagnosed with lower leg pain due to peripheral arterial disease by his physician. He began treatment with streptolysin O at a rate and amount of one (2 units/0.05 ml) drop, four times daily by sublingual administration. The treatment regimen has significantly decreased the leg pain and further improved his energy, ability to work, and improved his overall quality of life.

EXAMPLE 4

A 67-year old male was diagnosed with Dupuytren's contracture in one hand. He began treatment with streptolysin O at a rate and amount of one (2 units/0.05 ml) drop, four times daily by sublingual administration. After 14 days of treatment, the symptoms of the disease progressively reversed with each new treatment.

EXAMPLE 5

A 64-year old male was diagnosed with Dupuytren's contracture in both hands by his physician. He began treatment with streptolysin O at a rate and amount of one (2 units/0.05 ml) drop, four times daily by sublingual administration. After 14 days of treatment, the symptoms of the disease progressively reversed in both hands with each new treatment.

EXAMPLE 6

A 57-year old male patient was diagnosed with Peyronie's disease by his physician. He began treatment with steptolysin O at a rate and amount of one (2 units/0.05 ml) drop, three times daily by sublingual administration. After 30 days of treatment, improvements in the contracture of his penis were noted by the patient and their physician.

EXAMPLE 7

A male patient was diagnosed with Peyronie's disease by his physician. He began treatment with steptolysin O at a rate and amount of one (2 units/0.05 ml) drop, three times daily by sublingual administration. After 30 days of treatment, improvements in the contracture of his penis were noted by the patient and their physician.

EXAMPLE 8

Bovines, who have lost one or more quarters to mastitits were treated using one dose of streptolysin O (2 units/0.05 ml) drop, twice daily for thirty days by subcutaneous administration. The quarters damaged due to mastitis were reclaimed and produced milk after treatment.

Numerous modifications and variations in the practice of the invention are expected to occur to those skill in the art upon consideration of the presently preferred embodiments thereof. Consequently, the only limitations which should be placed upon the scope of the invention are those which appear in the appended claims.

What is claimed is:

1. A method of alleviating symptoms of a connective tissue disorder selected from the group consisting of Dupuytren's contracture, scleroderma, Peyronie's disease, and claudication due to peripheral arterial disease comprising administering to a subject in need thereof, streptolysin O in an amount effective to treat one or more symptoms of said connective tissue disorder.

2. The method of claim 1, wherein said connective tissue disorder is Dupuytren's contracture.

3. The method of claim 1, wherein said connective tissue disorder is scleroderma.

4. The method of claim 1, wherein said connective tissue disorder is Peyronie's disease.

5. The method of claim 1, wherein said connective tissue disorder is claudication due to peripheral arterial disease.

6. The method of claim 1, where said streptolysin O is administered by a mode selected from the group consisting of sublingual, bucal, oral drench, subcutaneous, intradermal, intravenous, intramuscular, intrathecal, inhalation, and topical.

7. The method of claim 6, wherein said streptolysin O is administered sublingually.

8. The method of claim 1, wherein said streptolysin O is administered at a dosage from about 0.0032 units to about 50 units.

9. The method of claim 1, wherein said streptolysin O is administered at a dosage from about 0.05 units to about 10 units.

10. The method of claim 1, wherein said streptolysin O is administered at a dosage from about 0.01 units to about 1.0 unit.

* * * * *